US009623102B2

(12) United States Patent
Hozbor et al.

(10) Patent No.: US 9,623,102 B2
(45) Date of Patent: Apr. 18, 2017

(54) VACCINES FOR THE PREVENTION OF INFECTIONS WITH *BORDETELLA*

(71) Applicants: CONSEJO NACIONAL DE INVESTIGACIONES CIENTIFICAS Y TECNICAS (CONICET), Buenos Aires (AR); UNIVERSIDAD NACIONAL DE LA PLATA, La-Plata-Buenos Aires (AR); INIS BIOTECH LLC, Milford, Kent County, DE (US)

(72) Inventors: Daniela Hozbor, Buenos Aires (AR); Daniela Bottero, La Plata-Buenos Aires (AR); María Emilia Gaillard, La Plata-Buenos Aires (AR); Eugenia Zurita, La Plata-Buenos Aires (AR); Maximiliano Omazabal, Bell-Buenos Aires (AR); Darío Flores, La Plata-Buenos Aires (AR); Agustina Errea, La Plata-Buenos Aires (AR); Griselda Moreno, La Plata-Buenos Aires (AR); Martin Rumbo, Bell-Buenos Aires (AR); Erika Bartel, La Plata-Buenos Aires (AR); Celina Castuma, La Plata-Buenos Aires (AR)

(73) Assignees: CONSEJO NACIONAL DE INVESTIGACIONES CIENTIFICAS Y TECHNICAS (CONICET), Buenos Aires (AR); UNIVERSIDAD NACIONAL DE LA PLATA, Buenos Aires (AR); INIS BIOTECH LLC, Milford, DE (US)

(*) Notice: Subject to any disclaimer, the term of this patent is extended or adjusted under 35 U.S.C. 154(b) by 0 days.

(21) Appl. No.: 14/780,677

(22) PCT Filed: Mar. 25, 2014

(86) PCT No.: PCT/IB2014/060143
§ 371 (c)(1),
(2) Date: Sep. 28, 2015

(87) PCT Pub. No.: WO2014/155294
PCT Pub. Date: Oct. 2, 2014

(65) Prior Publication Data
US 2016/0038582 A1 Feb. 11, 2016

(30) Foreign Application Priority Data
Mar. 27, 2013 (AR) .......................... P20130101023

(51) Int. Cl.
A61K 39/10 (2006.01)
A61K 39/02 (2006.01)
A61K 39/00 (2006.01)

(52) U.S. Cl.
CPC ........ *A61K 39/099* (2013.01); *A61K 39/0018* (2013.01); *A61K 2039/545* (2013.01); *A61K 2039/55505* (2013.01); *A61K 2039/55544* (2013.01); *A61K 2039/70* (2013.01)

(58) Field of Classification Search
None
See application file for complete search history.

(56) References Cited

PUBLICATIONS

Fattom et al. Vaccine vol. 17, No. 2, Jan. 1999, pp. 126-133(8).*
Abbas et al. Cellular and Molecular Immunology 4th edition chapter 15 p. 360-362, 2000.*
Ellis, R.W. (Chapter 29 of "Vaccines" [Plotkin, S.A. et al. (eds) published by W. B. Saunders company (Philadelphia) in 1988.*
International Search Report for International Application No. PCT/IB2014/060143 dated Jul. 31, 2014.
Roberts R, et al.: "Outer membrane vesicles as acellular vaccine against pertussis," Vaccine, Elsevier Ltd, GB, vol. 26, No. 36, Aug. 26, 2008 (Aug. 26, 2008), pp. 4639-4646, XP023613979.
Asensio Cristian J. A., et al.: "Outer membrane vesicles obtained from Bordetella pertussis Tohama expressing the lipid A deacylase PagL as a novel acellular vaccine candidate." Vaccine, vol. 29, No. 8, Feb. 11, 2011 (Feb. 11, 2011), pp. 1649-1656, XP002727134.
Wolfe Daniel N., et al.: "The O Antigen Enables Bordetella parapertussis to Avoid Bordetella pertussis-Induced Immunity," Infection and Immunity, vol. 75, No. 10, Oct. 2007 (Oct. 2007), pp. 4972-4979, XP002727133.
Bottero D, et al.: "Outer membrane vesicles derived from Bordetella parapertussis as an acellular vaccine against Bordetella parapertussis and Bordetella pertussis infection," Vaccine, vol. 31, No. 45, Oct. 25, 2013 (Oct. 25, 2013), pp. 5262-5268, XP002727135.
Gaillard Maria Emilia, et al.: "Acellular pertussis vaccine based on outer membrane vesicles capable of conferring both long-lasting immunity and protection against different strain genotypes," Vaccine, vol. 32, No. 8, Feb. 12, 2014 (Feb. 12, 2014), pp. 931-937, XP002727136.

* cited by examiner

*Primary Examiner* — Jennifer Graser
(74) *Attorney, Agent, or Firm* — Young & Thompson

(57) ABSTRACT

A vaccine for the prevention of infections with *Bordetella*, comprising at least outer membrane vesicles (OMVs) of *B. parapertussis*, excipients and/or adjuvants. *Bordetella* may be, for example, *B. pertussis* or *B. parapertussis*. The vaccine can comprise adjuvants, for example, aluminum hydroxide and other immunogens such as tetanus toxoid, diphtheria toxoid, or combinations thereof.
In another preferred embodiment, the vaccine for the prevention of infections with *Bordetella* comprises at least outer membrane vesicles (OMVs) of *B. pertussis* and the lipopolysaccharide of *B. parapertussis*, excipients and/or adjuvants. The vaccine can comprise between 3 to 20 μg per dose of OMVs from *B. pertussis* and between the amount equivalent to $10^7$ and $10^{10}$ bacteria per dose of lipopolysaccharide of *B. parapertussis*. The adjuvant can be aluminum hydroxide and other immunogens such as tetanus toxoid, diphtheria toxoid, or combinations thereof. The Tdap vaccine exhibits cross activity.

2 Claims, 15 Drawing Sheets

VACCINES FOR THE PREVENTION OF INFECTIONS WITH *BORDETELLA*

FIELD OF THE INVENTION

This invention refers to the field of vaccines; in particular, it refers to vaccines against bacterial pathogens. This invention refers to outer membrane vesicles (OMVs) derived from bacteria comprising protein and non-protein components that can be pharmaceutical products for human and/or veterinary uses, particularly for the formulation of acellular vaccines against *Bordetella pertussis* and *B. parapertussis* (the etiological agents of the disease known as whooping cough or pertussis). OMVs isolated from these bacteria can be used as vaccines with a single component or monovalent; or combined or multivalent vaccines. For example, they can be used combined with tetanus and diphtheria toxoids.

BACKGROUND OF THE INVENTION

Whooping cough (or pertussis) is a current problem in public health and an important cause of death among children, including countries with a high level of vaccination. This is a bacterial disease mainly caused by *Bordetella pertussis*, and also by *B. parapertussis*. Estimates by the World Health Organization (WHO) indicate that in 2008 there were close to 16 million cases of whooping cough worldwide, 95% of which were located in developing countries, and around 195,000 children have died as a result of this disease.

Child immunization programs with a vaccine against whooping cough have been successful in preventing a serious disease. But in the last decades, the disease has reappeared with characteristic outbreaks occurring every two to three years, with a surprisingly high number of cases not only among the infant population, but also among adolescents and adults.

The scientific community and healthcare professionals have focused their activities on the search to ascertain the causes for the resurgence of the disease, as well as on the review and application of new strategies to enhance disease control. As to the causes that might explain this resurgence of the disease, various explanations have been proposed, most of which are related to the vaccines currently in use (He, Q., J. Makinen, et al. J. Infect. Dis. 187:1200-1205, 2003 and Mooi, F. R., et al. Emerg. Infect. Dis. 7:526-528, 2001).

In this context, besides optimizing the use of existing vaccines, the development of new and enhanced vaccines is urgent. In this regard, it is important to remember that there are two types of vaccines: a) cellular vaccines constituted by a suspension of whole bacteria destroyed by heat and detoxified: b) acellular vaccines (also known as subunit vaccines) consisting of purified protein immunogens (3 or 5) of *B. pertussis*. There are pediatric formulations for acellular vaccines, as well as formulations aimed at adolescents and adults. It is important to point out that none of the present day formulations contain any components deriving from *B. parapertussis*. Moreover, these formulations do not confer any adequate protection against this etiological agent of the whooping cough (Cherry, J. D., et al. 2008-2010. Clin. Infect. Dis. 54:534-53715).

Subunit vaccines (nonreplicative systems, also known as acellular vaccines) are particularly attractive among traditional vaccine designs, given that they induce a protective immune response, thus avoiding the limitations on biosafety of any of the attenuated vaccines or vaccines made of whole dead microorganisms. Despite its advantages in terms of safety, a major limitation of subunit antigens is their inability to stimulate strong in vivo immune responses when administered alone.

BRIEF DESCRIPTION OF THE INVENTION

A vaccine for the prevention of infections with *Bordetella* is provided, comprising at least outer membrane vesicles (OMVs) of *B. parapertussis*, excipients and/or adjuvants. *Bordetella* may be, for instance, *B. pertussis* or *B. parapertussis*. The vaccines may comprise adjuvants, e.g., aluminum hydroxide, in addition to tetanus toxoid, diphtheria toxoid, or combinations thereof.

Another preferred embodiment is provided, comprising a vaccine for the prevention of infections with *Bordetella*, comprising at least outer membrane vesicles (OMVs) of *B. pertussis* and the lipopolysaccharides of *B. parapertussis*, excipients and/or adjuvants. OMVs comprise at least one protein, e.g., at least one of the proteins listed in Tables 1 and 2, or combinations thereof. *Bordetella* may be *B. pertussis* and *B. parapertussis*. The vaccine can also comprise between 3 to 20 pig/per dose of OMVs of *B. pertussis* and between the equivalent contained in $10^7$ to $10^{10}$ bacterias per dose of the lipopolysaccharide of *B. parapertussis*. The adjuvant can be aluminum hydroxide. OMV-based vaccines can be combined with tetanus toxoid and diphtheria toxoid.

In another embodiment, a vaccine for the prevention of infections with *Bordetella* is provided, comprising outer membrane vesicles (OMVs) of *B. pertussis* and outer membrane vesicles (OMVs) of *B. parapertussis*, excipients and/or adjuvants. The adjuvant can be aluminum hydroxide and can be added to the tetanus toxoid and diphtheria toxoid formulations, or combinations thereof. In another preferred embodiment, the vaccine comprises between 0.75 and 3 µg of outer membrane vesicles (OMVs) of *B. pertussis*, between 3 and 9 µg of outer membrane vesicles (OMVs) of *B. parapertussis*, 5 to 7 Lf per dose of tetanus toxoid, 1 to 3 Lf per dose of diphtheria toxoid, and less than 1.25 mg per dose of aluminum.

Figure 6:
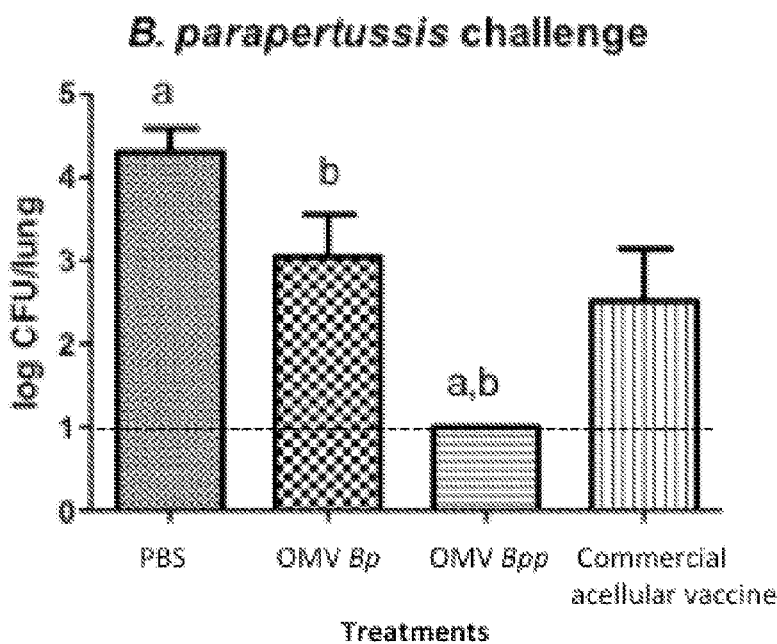

FIG. 6: Immunization with OMVs derived from *B. parapertussis* (3 µg per dose) confers maximum protection against an intranasal challenge by *B. parapertussis*. *B. parapertussis* AR729 was used for the challenges ($1 \times 10^7$ CFU 40 $\mu l^{-1}$). Three independent experiments were performed. The results of a representative experiment from the series are shown here. These results correspond to the mean from a lot of five animals for each condition. Counting was carried out on day seven post-challenge. The dashed line indicates the detection limit of the assay under the conditions in which it was performed. Bacterial counting is expressed as the group mean±standard error. a and b p<0.001.

Figure 7:
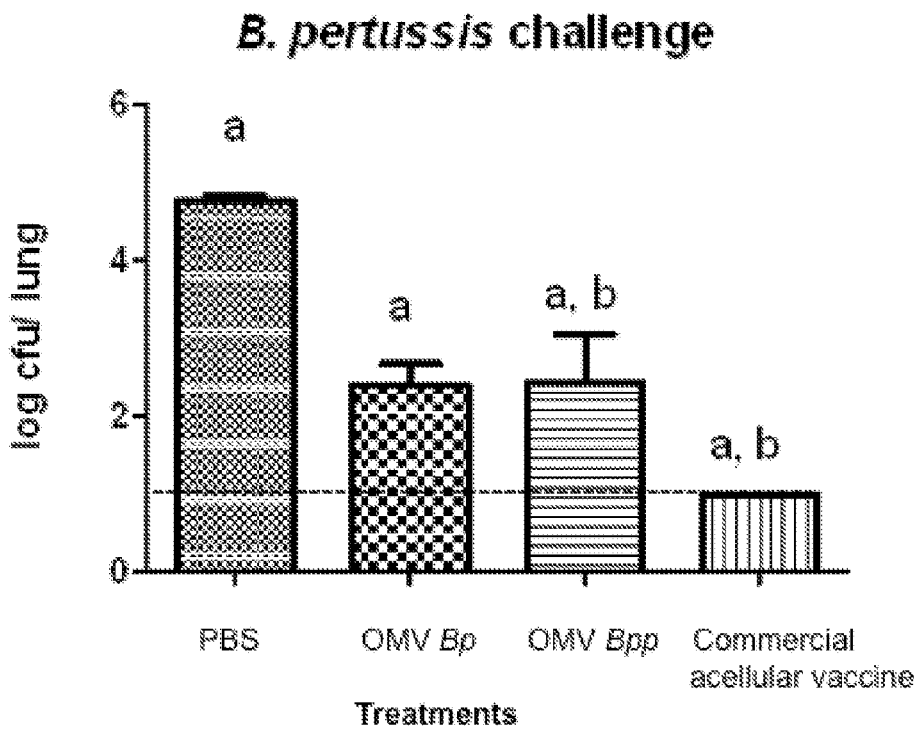

FIG. 7: FIG. 7 shows the protective capacity of OMVs from *B. pertussis* (3 µg per dose), OMVs from *B. parapertussis* (3 µg per dose) and a commercial acellular vaccine under an intranasal immunization model. The strain *B. pertussis* 18323 was used for the challenges at a dose of $2 \times 10^7$ CFU 40 $\mu l^{-1}$. Three independent experiments were carried out. The results of a representative experiment from the series are shown here. These results correspond to the mean from a lot of five animals for each condition. Counting was performed on day seven post-challenge. The dashed line indicates the detection limit of the assay under the conditions in which it was carried out. Bacterial counting is expressed as the group mean±standard error. a and b p<0.001.

Figure 8:
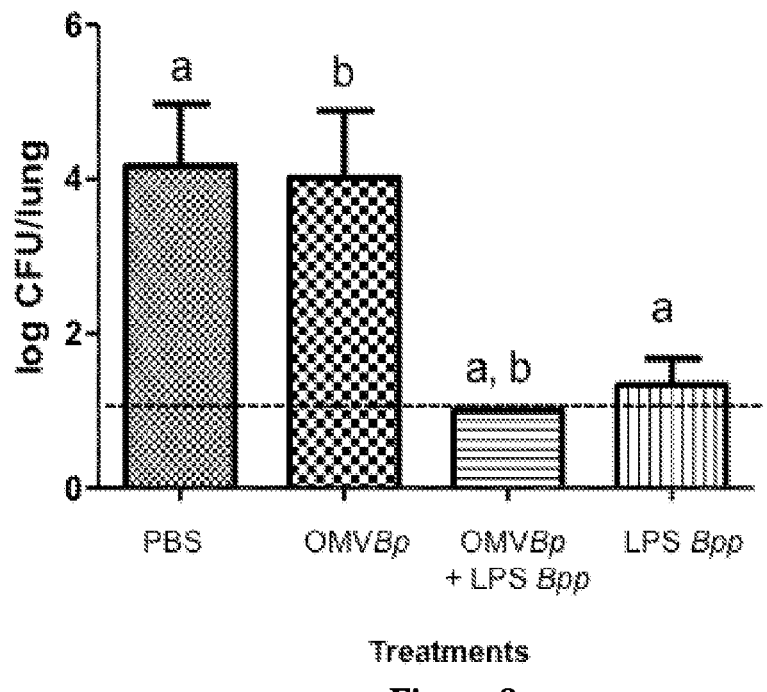

FIG. 8: The protective capacity of OMVs from *B. pertussis* (3 µg per dose)+LPSBpp (1 µg per dose) in the intranasal challenge model with *B. parapertussis*. The strain *B. parapertussis* AR729 was used for the challenges ($2.8 \times 10^7$ CFU 40 $\mu l^{-1}$). Results obtained from mice immunized with OMVs of only *B. pertussis* or LPS of only Bpp are included. Three independent experiments were carried out for each case. The results of a representative experiment from the series are shown here. These correspond to the mean from a lot of five animals for each condition. Counting was performed on day seven post-challenge. The dashed line indicates the detection limit of the assay under the conditions in which it was carried out. Bacterial counting is expressed as the group mean±standard error. a and b p<0.001.

Figure 9:
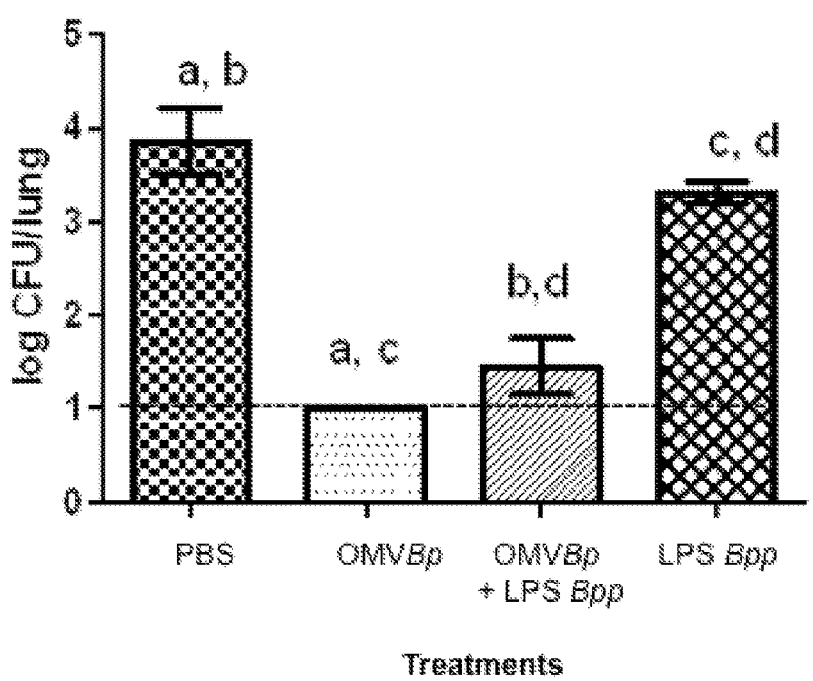

FIG. 9: The protective capacity of OMVs from *B. pertussis* (3 µg per dose)+LPSBpp (1 µg per dose) under an intranasal challenge model with *B. pertussis*. *B. pertussis* 18323 was used in the challenge ($6 \times 10^6$ CFU 40 $\mu l^{-1}$). Results obtained from mice immunized with OMVs *B. pertussis* alone or LPS Bpp alone. Three independent experiments were carried out for each case. The results of a representative experiment from the series are shown here. These results correspond to the mean from a lot of five animals for each condition. Counting was performed on day seven post-challenge. The dashed line indicates the detection limit of the assay under the conditions in which it was carried out. Bacterial counting is expressed as the group mean±standard error. a and b p<0.001.

Figure 10:
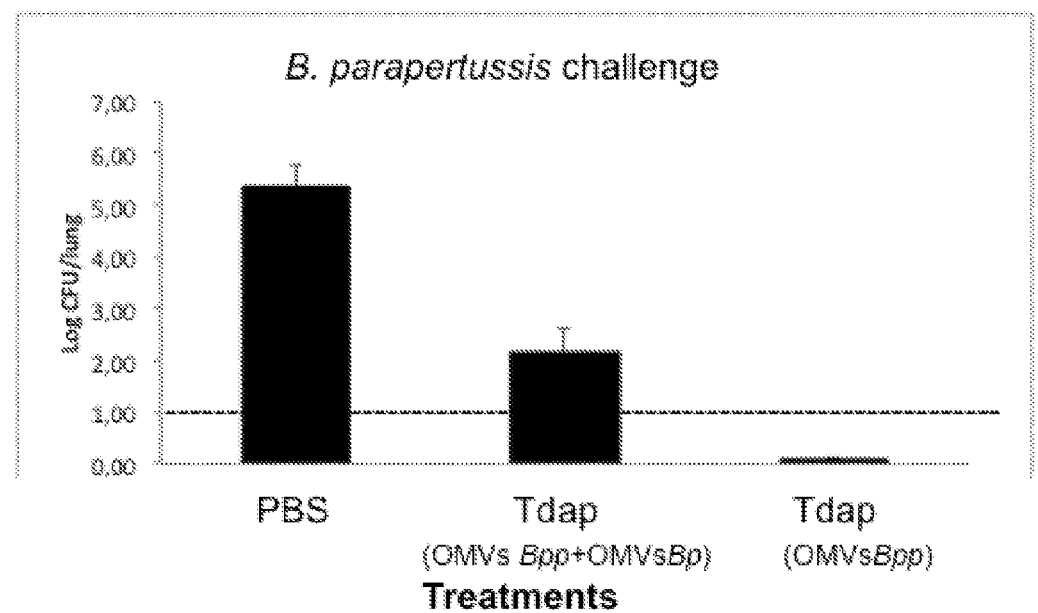

FIG. 10: The protective capacity of acellular triple vaccines containing OMVs from *Bordetella pertussis* and *B. parapertussis*, tetanus toxoid and diphtheria toxoid (Tdap$_{OMVsBpp+OMVsBp}$). The strain *B. parapertussis* AR729 was used ($1 \times 10^7$ CFU 40 $\mu l^{-1}$) as a challenge strain. Results obtained from mice immunized with OMVs of only *B. parapertussis* were also included. In all cases, three independent experiments were performed. The results of a representative experiment from the series are shown here. These results correspond to the mean from a lot of five animals for each condition. Counting was performed on day seven post-challenge. The dashed line indicates the detection limit of the assay under the conditions in which it was carried out. Bacterial counting is expressed as the group mean±standard error.

Figure 11:
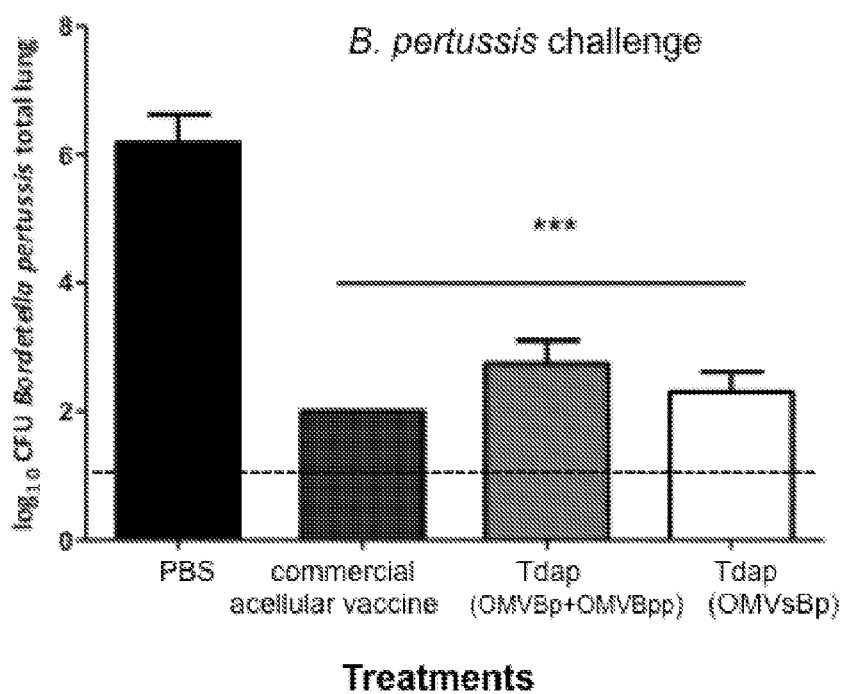

FIG. 11: The protective capacity of acellular triple vaccines containing OMVs from *Bordetella*, tetanus toxoid and diphtheria toxoid (Tdap$_{OMVsBpp+OMVsBp}$). A suspension of *B. pertussis* ($2 \times 10^7$ CFU 40 $\mu l^{-1}$) was used for the challenge. Results obtained from mice immunized with OMVs of only *B. pertussis* or a commercial acellular vaccine are included. In all cases, three independent experiments were performed. The results of a representative experiment from the series are shown here. These results correspond to the mean from a lot of five animals for each condition. Counting was performed on day seven post-challenge. The dashed line indicates the detection limit of the assay under the conditions in which it was carried out. Bacterial counting is expressed as the group mean±standard error.

Figure 12:
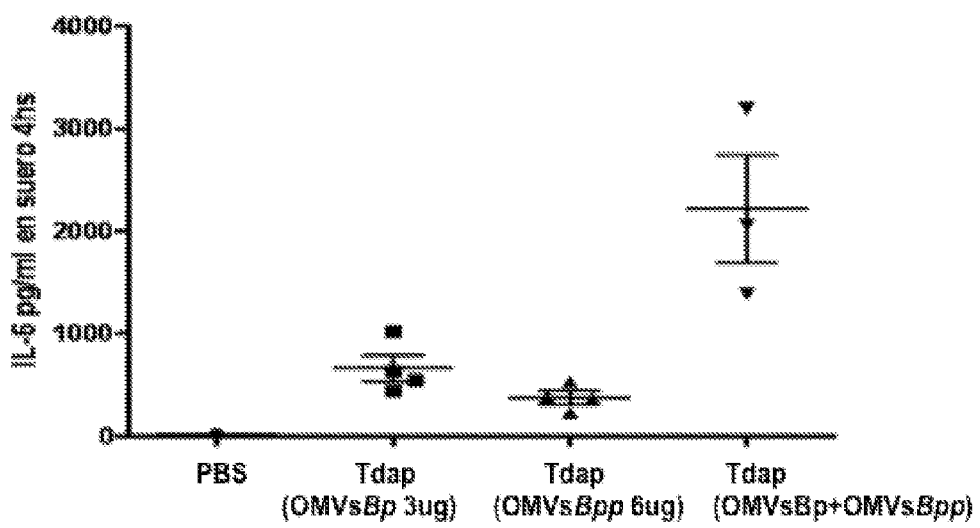

FIG. 12: IL6 levels in serum after the immunization of mice with Tdap$_{OMVsBp}$. Tdap$_{OMVsBpp}$ or Tdap$_{OMVsBp+OMVsBpp}$. Four hours after immunization, serum from the treated animals was collected and IL6 was measured by ELISA. The results show the mean and standard deviation of individual measurements. The control group was treated with PBS s.c.

Figure 13:
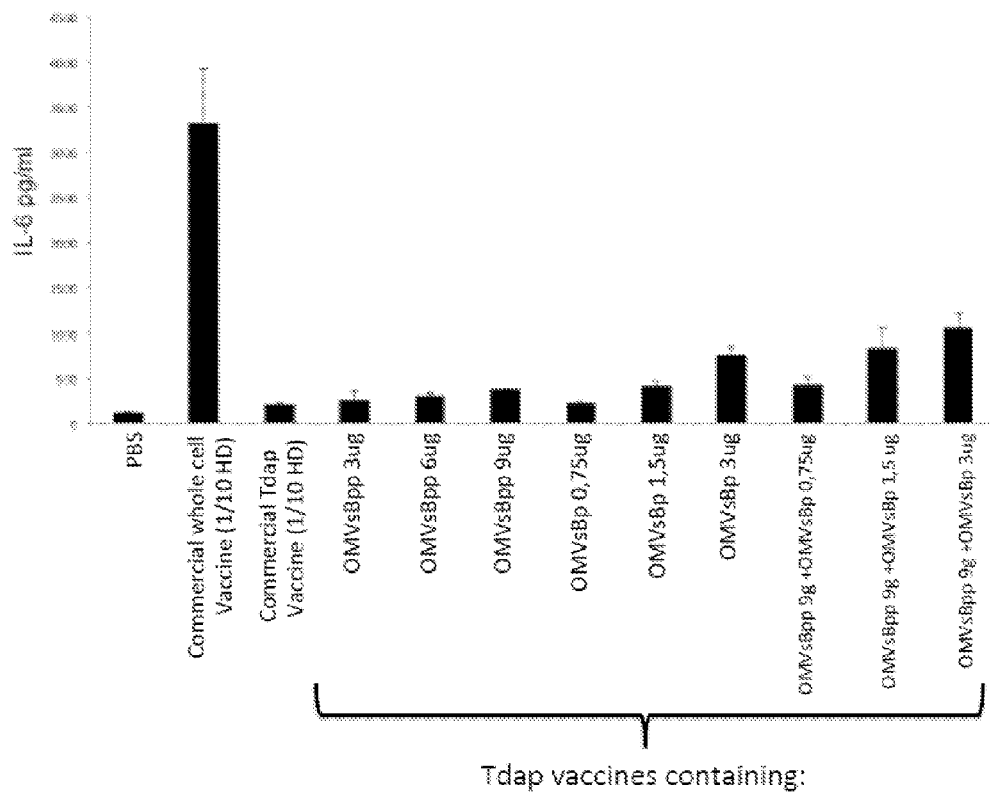

FIG. 13: IL6 levels in serum after immunization of mice with Tdap$_{OMVsBp}$, where the content of OMVsBp used was 3; 1.5 or 0.75 µg; Tdap$_{OMVsBpp}$, where the content of OMVsBpp used was 3, 6 or 9 µg; or Tdap$_{OMVsBp+OMVsBpp}$ with the following combinations of OMVsBp and OMVsBpp: 3 µg:9 µg; 1.5 µg:9 µg and 0.75 g:9 µg. Four hours after immunization, serum from the treated animals was collected and IL6 was measured by ELISA. Results show the mean and standard deviation of individual. The commercial cellular and acellular vaccines were used as controls. PBSs.c. treatment corresponded to the assay negative control.

Figure 14:
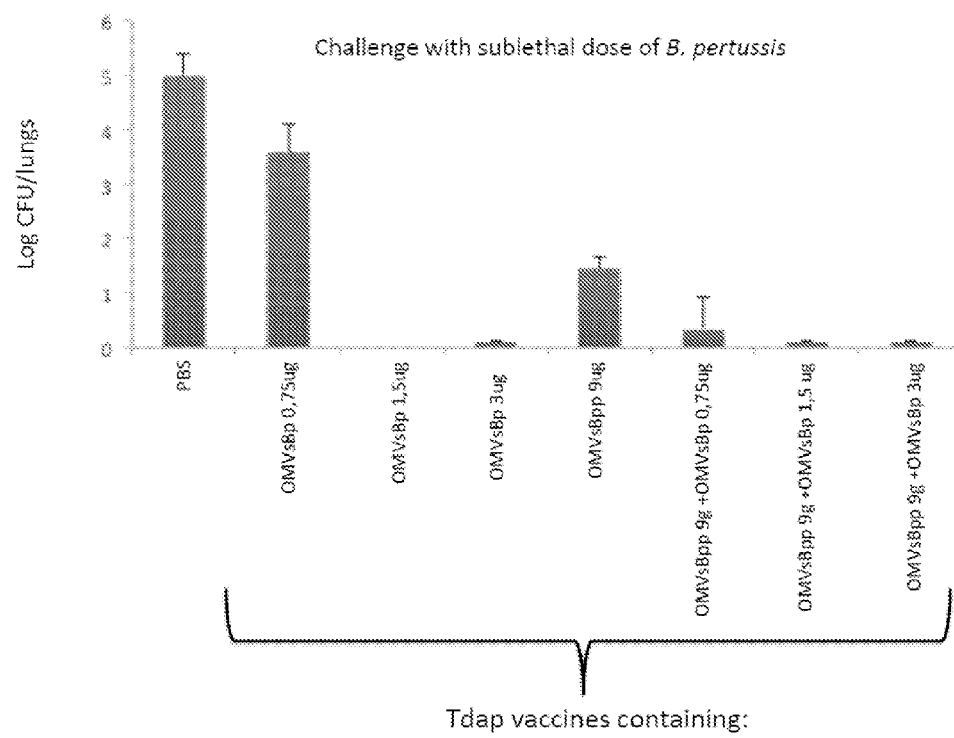

FIG. 14: Protective capacity of acellular triple vaccines containing OMVs from *B. pertussis* and from *B. parapertussis* in different concentrations combining tetanus toxoid and diphtheria toxoid (TdapOMVsBpp+OMVsBp). The combinations assayed were 9 µg of OMVs from Bpp with the following quantities of OMVs Bp 0.75 µg, 1.5 µg and 3 µg. A suspension of *B. pertussis* ($2 \times 10^7$ CFU 40 $\mu l^{-1}$) was used for the challenge. Results obtained from mice immunized with Tdap vaccines containing only OMVsBp in concentrations of 0.75 µg, 1.5 µg or 3 µg, or with Tdap vaccines containing only 9 µg of OMVsBpp are included. Mice treated with PBS were used as a negative control for protection. In all cases, three independent experiments were performed. The results from an experiment representative of the series are shown here. The results shown correspond to the mean of a batch of 5 animals for each condition. Counting was performed on day 7 post-challenge. The dashed line indicates the assay limit of detection under the conditions in which the experiment was carried out. The bacterial count is expressed as the group mean±standard error.

Figure 15:
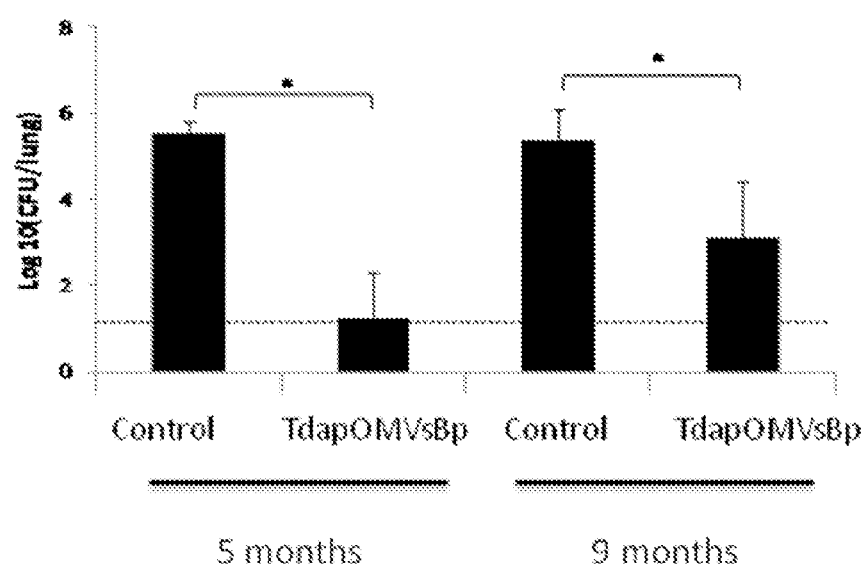

FIG. 15: FIG. 15 illustrates the long-term protective capacity of the Tdap vaccine (OMVsBp). The animals were subjected to an immunization plan consisting of two doses administered two weeks apart, using a formulation based on OMVBp (3 µg), DT (1 to 3 Lf per dose with a dose strength of 0.1 UIA per ml of serum) and TT (5 to 7 LF per dose with a dose strength greater than or equal to 2 UIA of serum per ml), using aluminum hydroxide as an adjuvant. At months 5 and 9 post-immunization, the animals were challenged intranasally with a sublethal dose of B. pertussis 18323 ($10^6$-$10^8$ CFU 40 $\mu l^{-1}$). The figure shows the average lung counts and the standard deviation for each group (n=5) on day 7 post-challenge. The dashed line indicates the limit of detection at counting. The results shown are representative of three independent experiments. * $p<0.05$.

Figure 16:
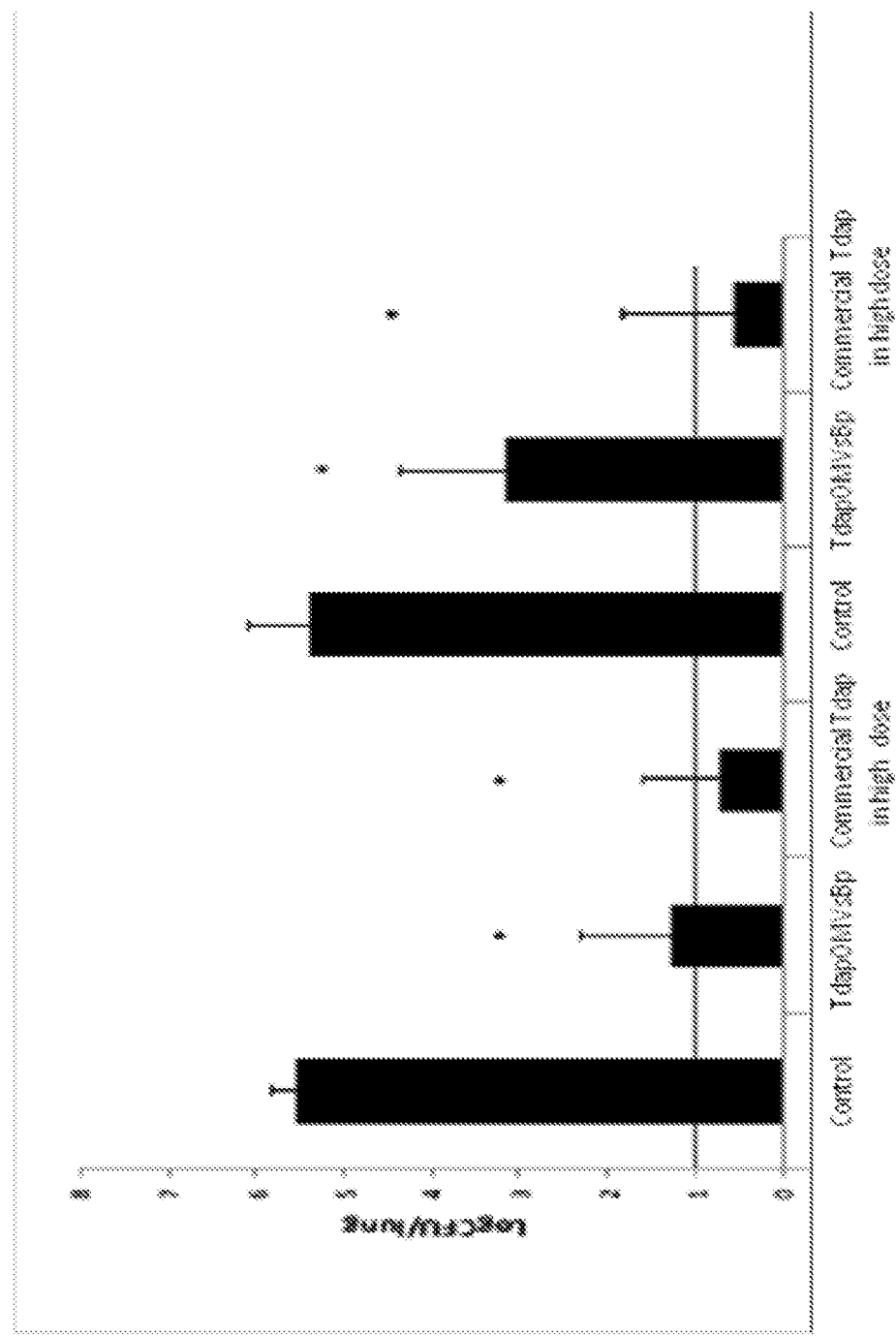

FIG. 16: Long-lasting immunity induced in TdapOM-VsBp-vaccinated mice. Immunization protocols comprised a two-dose schedule over a period of 2 weeks. Mice were challenged 5 and 9 months after the second immunization by nasal challenge with i.n.sublethal dose of Bp18323. These experiments were designed in a way to make the challenge at the same time and with the same dose of B. pertussis. Three independent experiments were performed. Results from one representative experiment are shown. Results depicted are the means of five mice per group on day 7 post-challenge. The dashed line indicates the lower limit of detection. Bacterial numbers are expressed as the log±SD. *$p<0.05$.

Figure 17:
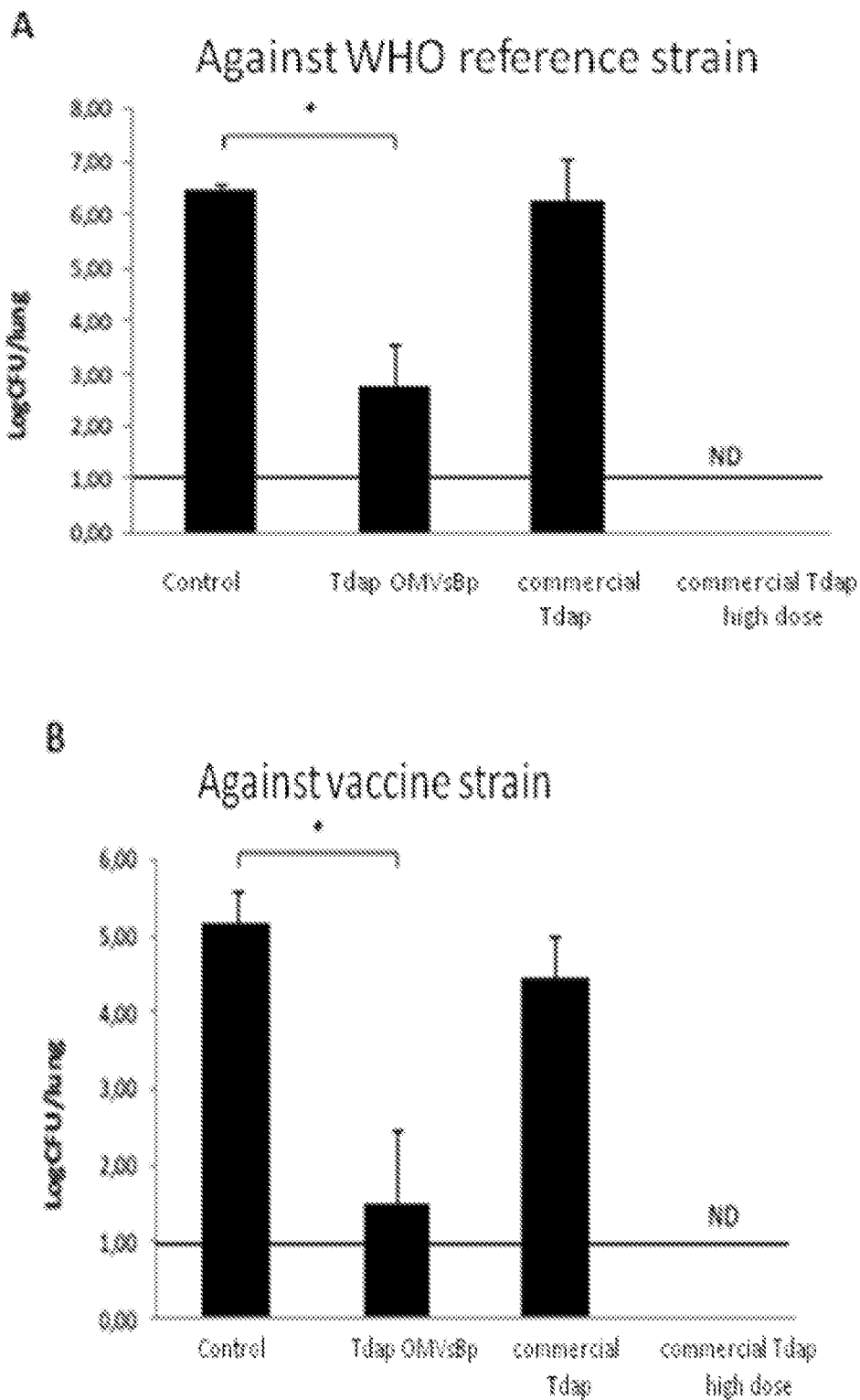
Figure 17:
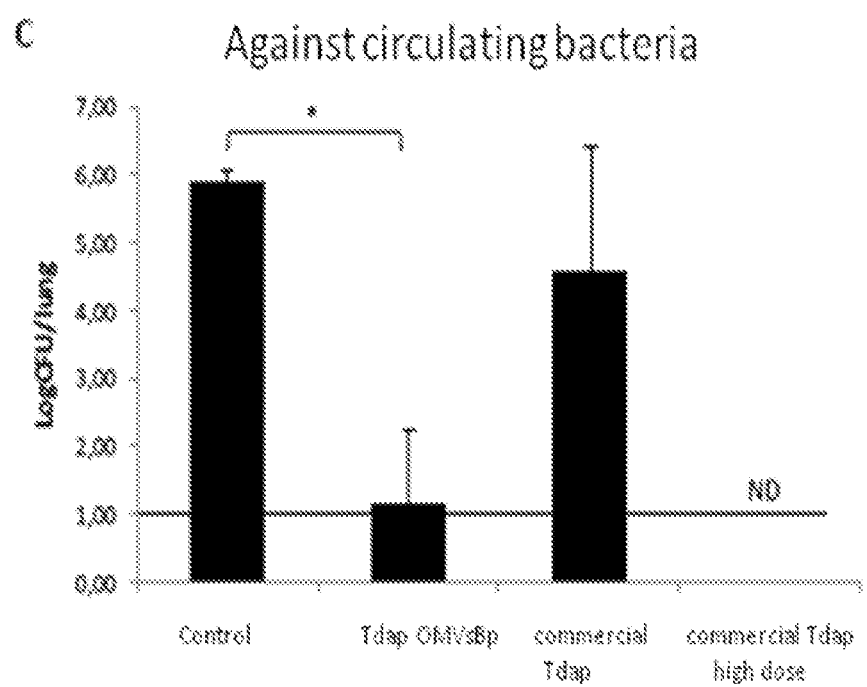

FIG. 17: Effect of immunization with TdapOMVsBp and commercial Tdap vaccine in the mouse intranasal challenge model. A commercial Tdap vaccine was used in two different doses, one corresponded to a high dose. Immunization protocols comprised a two-dose schedule over a period of 2 weeks. Mice were challenged 2 weeks after the second immunization by nasal challenge with a sublethal dose of WHO reference strain Bp 18323 (Panel A), the vaccine strain Tohama phase I (Panel B), or the circulating bacteria Bp106 (Panel C). Three independent experiments were performed. Results from one representative experiment are shown. Results depicted are the means of five mice per group at day 7 post-challenge. The dashed line indicates the lower limit of detection. Bacterial numbers are expressed as the log±SD. *$p<0.001$. ND: Not Detected.

A DETAILED DESCRIPTION OF THE INVENTION

The invention discloses outer membrane vesicles (OMV), also known as nanoparticles, from different species of the genus *Bordetella*, and in particular, the ones derived from *B. parapertussis* (OMVsBpp) and *B. pertussis* (OMVsBp), as adequate vaccines against whooping cough.

Outer membrane vesicles comprise many proteins from the outer membrane (more than 70 different proteins) and lipopolysaccharides. These components contribute to the antigenic profile of the bacteria.

OMVs derived from *B. pertussis* and *B. parapertussis* can be used to prepare vaccines with OMVs as the single immunogenic component or in combination with other immunogens. For example, OMVs can be used combined with diphtheria and tetanus toxoids.

OMVs derived from wild strains or recombinant strains of *B. pertussis* can be used in the preparation of vaccines with OMVs as the single immunogenic component or in combination with other immunogens in order to be protective against infections caused by *B. pertussis*.

One advantage shown in this invention is that OMVs derived from *B. parapertussis* when used to prepare vaccines used as a single immunogenic component or combined with other immunogens are capable of inducing protective immunity against *B. parapertussis*, but also against *B. pertussis*.

In addition, the combination of vaccines of OMVs deriving from *B. pertussis* with OMVs deriving from *B. parapertussis* and diphtheria and tetanus toxoids exhibit the capacity to adequately protect against the disease caused by *B. pertussis* and *B. parapertussis*.

The addition of LPS from *B. parapertussis* in formulations that only contain OMVs deriving from *B. pertussis* makes vaccines containing OMVs from *B. pertussis* exhibit protective capacities against *B. parapertussis* and *B. pertussis*.

This invention also refers to the production methods of OMVs isolated from *Bordetella* and to the various vaccine formulations containing such OMVs.

The isolated OMVs can be produced by recombinant strains of *Bordetella*, which express a modified structure of the lipopolysaccharide (LPS).

With the purpose of facilitating an understanding of this invention, a number of terms used in this invention are defined in more detail as follows.

Definitions

The term "pathogen" is used herein to refer to an organism that can cause disease in humans and/or animals.

For the purpose of this invention. "outer membrane vesicles" (OMVs) are defined as small particles deriving naturally from bacterial cells, consisting of protein and non-protein bacterial components. Gram-negative bacteria, especially pathogenic ones, usually secrete OMVs during infections in a process known as formation of appendices. OMVs also can be obtained by a number of physical and chemical processes described in detail hereunder.

The term "vaccine" that is referred to herein is defined as a pharmaceutical or therapeutic composition or formulation used to inoculate animals (humans in the future) with the purpose of immunizing them against a disease caused by pathogens.

For the purposes of this invention, the term "acellular vaccine" is defined as non-replicant systems that induce an immune protective response avoiding the safety limitations that any vaccine that has been attenuated or formulated from whole dead microorganisms entails.

For the purposes of this invention, "OMVsBpp" means outer membrane vesicles of *B. parapertussis* and "OMVsBp" means outer membrane vesicles of *B. pertussis*.

For the purposes of this application, the phrase "vaccine with a single component" is interchangeable and has the same meaning as the phrase "monovalent vaccine".

For the purposes of this application, the phrase "combined vaccine" is interchangeable and has the same meaning as the phrase "multivalent vaccine".

Figure 1:
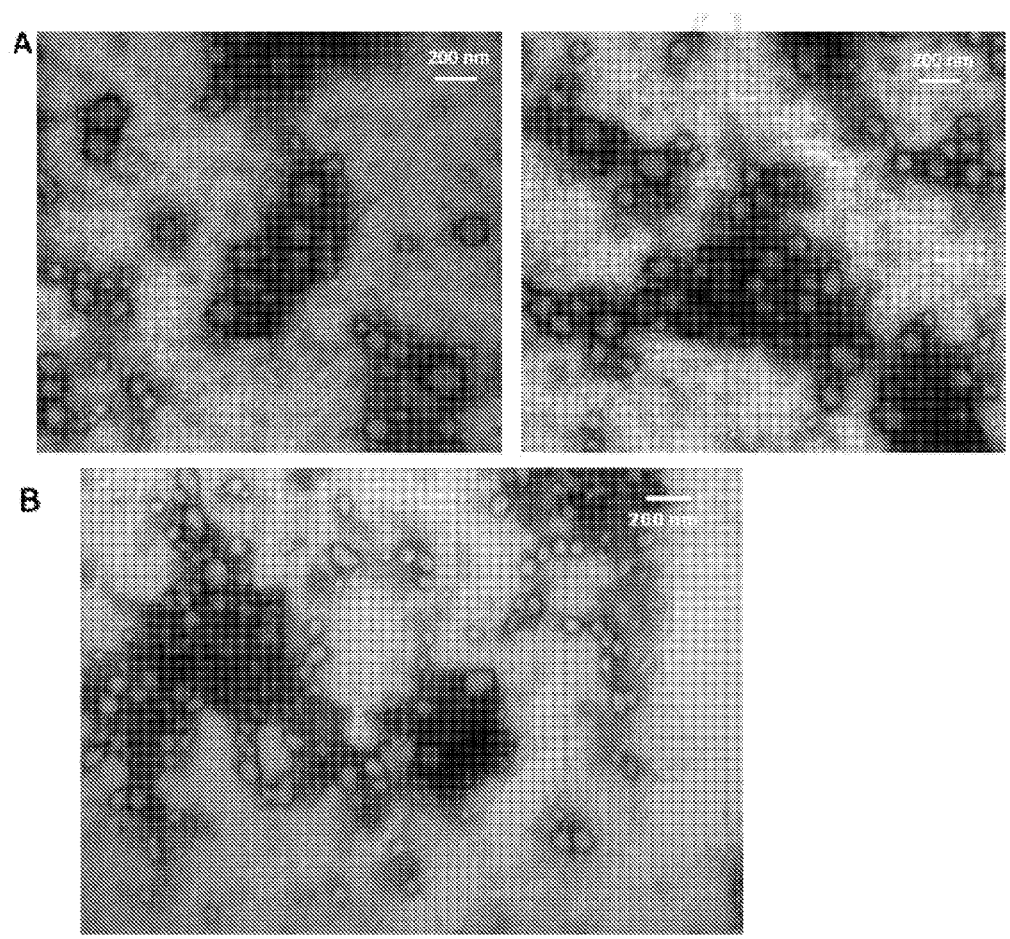
FIG. 1. Electron microscopic images of the outer membrane vesicles of *B. parapertussis* (Bpp. Panel A) and *B. pertussis* (Bp, Panel B).

OMVs were obtained following the procedure described in the examples. The samples obtained from either *B. pertussis* Tohama or *B. parapertussis* AR729 were stained negatively and then examined by electron microscopy. Some of the images obtained are shown in FIG. 1.

To advance in the characterization of OMVs, 2D electrophoresis was performed associated with mass spectrometry, which enabled the identification of some of the proteins present in OMVs. The locations of the identified proteins (Tables 1 and 2) were predicted within the bacterial cell by means of the PSORTb algorithm. Proteins with a cytoplasmic location, such as EF-Tu, TS ET, enolase, chaperonin 60-kDa and some dehydrogenases seem to be associated with membranes as observed in *Neisseria meningitidis*.

Table 1
1. Outer Membrane Porin
2. Co-chaperonin GroES
3. Dihydrolipoamide Dehydrogenase [*Bordetella parapertussis* 12822]
4. Universal Stress Protein [*Bordetella parapertussis* 12822]
5. Chaperonin GroEL 6. Serine Protease
7. Elongation Factor Tu
8. Outer Membrane Porin OmpQ [*Bordetella parapertussis* Bpp5]
9. Surface Antigen [*Bordetella parapertussis* Bpp5]
10. ATP-dependent Protease (subunit) [*Bordetella parapertussis* 12822]
11. Iron-sulfur Protein of Succinate Dehydrogenase [*Bordetella parapertussis* Bpp5]
12. Enoyl-ACP Reductase [*Bordetella parapertussis* 12822]
13. Autotransporter [*Bordetella parapertussis* 12822]
14. Translocation Protein TolB [*Bordetella parapertussis* 12822]
15. Outer Membrane Porin [*Bordetella parapertussis* 12822]
16. Biotin Carboxylase [*Bordetella parapertussis* 12822]
17. Gamma-glutamyl Transpeptidase [*Bordetella parapertussis* 12822]
18. Pertactin Precursor BPP1150

Figure 2:
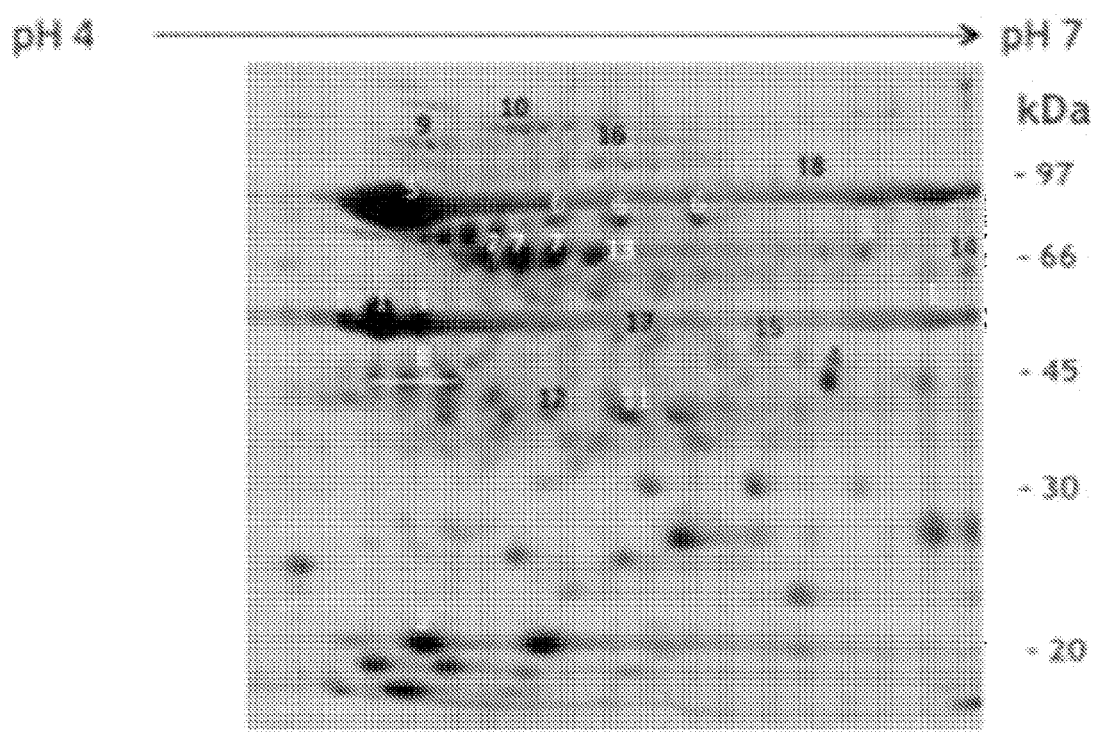
FIG. 2. Proteomes of the OMVs derived from *B. parapertussis*. The protein samples were separated by first-dimensional IEF in the pH range between 4 and 7 and afterward by second-dimensional SDS-PAGE at 12.5%. Proteins were visualized by Coomassie colloidal staining. The numbers refer to the peptide subunits identified by mass spectrometry, as described in Table 1.
Figure 3:
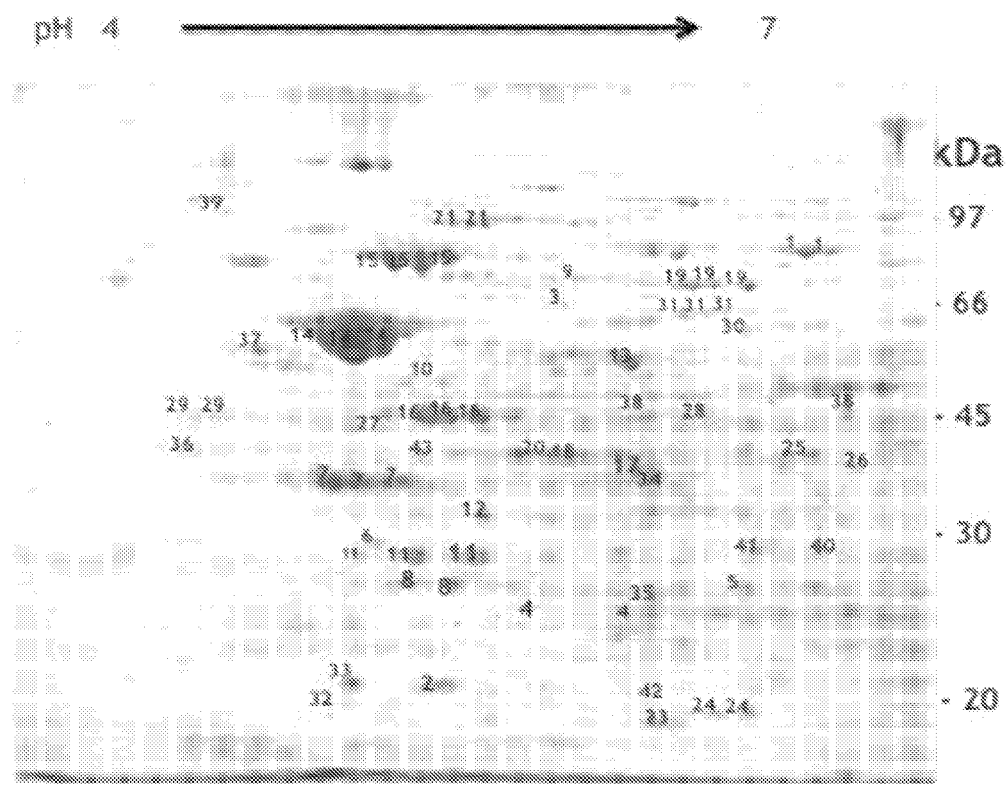
FIG. 3. Proteomes from OMVs derived from *B. pertussis*. Protein samples were separated by first-dimensional IEF in the pH range between 4 and 7 and afterward by second-dimensional SDS-PAGE at 12.5%. Proteins were visualized by Coomassie colloidal staining. The numbers refer to the peptide subunits identified by mass spectrometry, as described in Table 2.

Table 2
1. Putative Outer Membrane Protein
2. Conserved Hypothetical Protein BP3441
3. Hypothetical Protein BP3128
4. Putative Lipoprotein BP1296
5. Catalytic Subunit of Succinate Dehydrogenase BP2360
6. Outer Membrane Protein OMPQ
7. Precursor of the Outer Membrane Porin Protein BP0840
8. Putative ABC Transporter ATP-binding Protein BP3757
9. N Utilization Substance Protein A BPI 246
10. Arginine Synthetase BP3537
11. Putative Membrane Protein BP1440
12. Glutathione Synthetase BP1499
13. Serine Protease BP2434
14. Chaperonin 60 kDa BP3495
15. Serum Resistance Protein BP3494
16. Elongation Factor Tu BP0007
17. Fructose-bisphosphate Aldolase BP1519
18. DNA-directed RNA Polymerase Subunit Alpha BP3642
19. Pertactin BP1054
20. Putative Quinone Protein BP2196
21. ATP-dependent Protease Subunit ATPasa BP1198
22. Polysaccharide Biosynthesis Protein BP3150
23. Outer Membrane Protein A Precursor BP0943
24. Superoxide Dismutase BP2761
25. Aspartate Aminotransferase BP1795
26. Putative Binding Protein Transporter-dependent BP3322
27. Dihydrolipoamide Acetyle Dehydrogenase BPI 125
28. Exported Putative Solute-binding Protein BP2963
29. Enolase BP2386
30. Serum-resistant Protein BP3494
31. Succinate Dehydrogenase Flavo Protein Subunit BP2361
32. Alkyl Hydroperoxide Reductase BP3552
33. Lipoprotein BP2750
34. Putative ABC Transport Solute-binding Protein BP2747
35. Enoyl-acyl Carrier Protein BP3215
36. Hypothetical Protein BP3559
37. Trigger Factor BP1774
38. Hypothetical Protein BP1203
39. Ligand-binding Putative Outer Membrane Protein
40. Aconitase Hydrolase
41. Hypothetical Protein BP2818
42. Transcription Antitermination Protein, NusG
43. Succinyl-CoA Synthetase Subunit Beta Some of the proteins separated by 2D electrophoresis displayed multiple spots with different pH values (horizontal stains) (FIGS. 2 and 3). These variations in loading were observed in proteins such as EF-Tu, chaperonin 60-kDa, outer membrane porin protein, resistance to the serum protein, and serine protease. Multiple spots may represent natural isoforms, or an artifact caused by the sample preparation itself. The serum resistance protein was resolved in multiple spots with different weights that may result from protein processing, its degradation, and/or modifications (FIG. 3).

The outer membrane proteins detected were pertactin, the outer membrane porin precursor, OMPQ. Other identified proteins may be implicated in carbohydrate metabolism.

Figure 4:
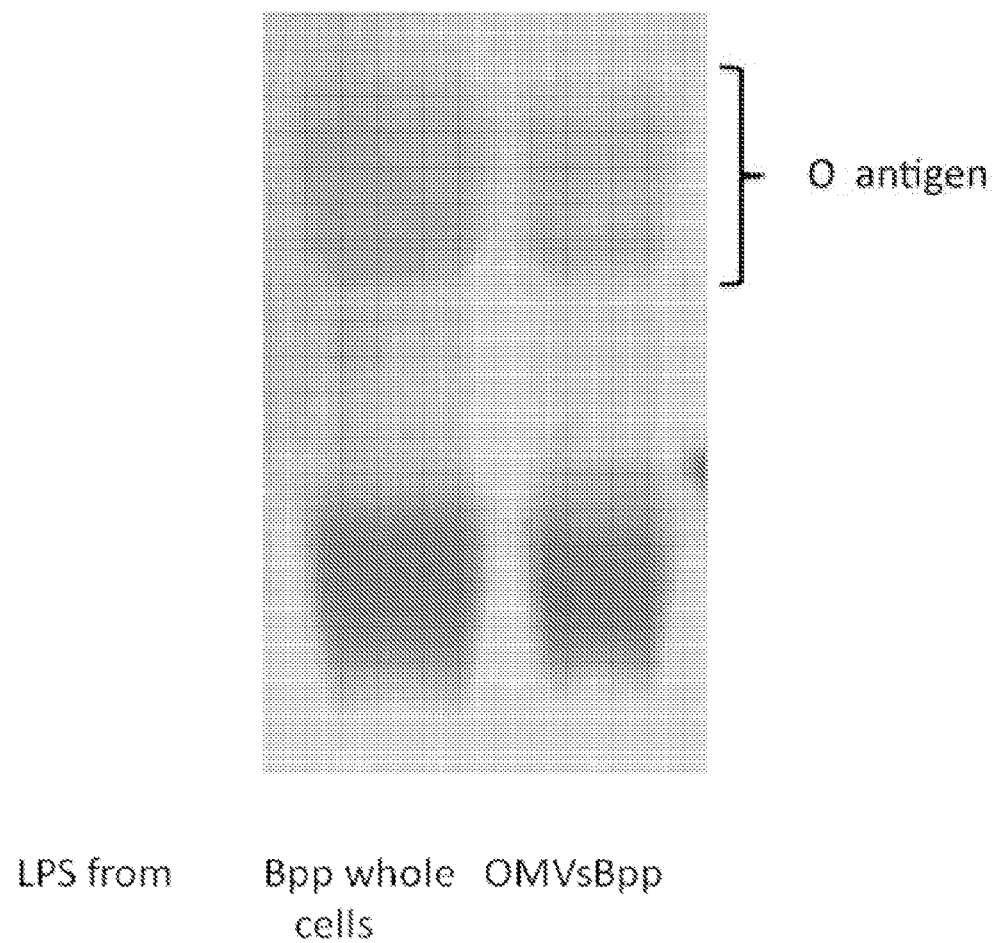
FIG. 4: The electrophoretic run (SDS-PAGE) of lipopolysaccharides of *B. parapertussis*. LPS of OMVs from *B. parapertussis* were solubilized in the loading buffer and heated at 100° C. for 10 min. LPS was visualized by silver staining (BioRad).
Figure 5:
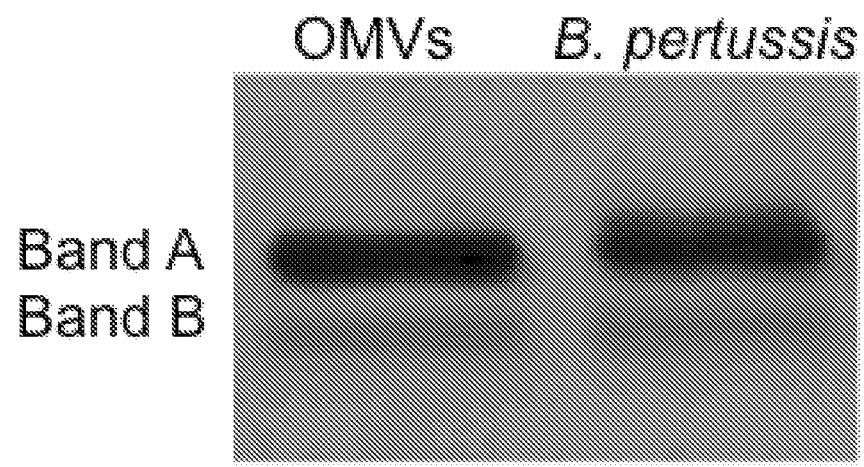
FIG. 5: The electrophoretic run (SDS-PAGE) of lipo-oligosaccharides (LOS) of *B. pertussis*. The OMVs of *B.* pertussis were solubilized in the loading buffer and heated at 100° C. for 10 min. LOS was visualized by silver staining (BioRad).

The profiles of lipopolysaccharides of OMVs obtained from *B. parapertussis* and *B. pertussis* are different (FIGS. 4 and 5). The LPS of *B. parapertussis* contains the antigen O composed of a homopolymer of 2,3-dideoxy-2,3-di-N-acetyl galactosaminuronic acid (FIG. 4). Furthermore, the LOS of *B. pertussis* lacks the O antigen. There is a trisaccharide in its place (FIG. 5). The LOS extracted from whole cells was included in the gel and in FIG. 5. The LOS of *B. pertussis* was resolved in two bands, bands A and B. The two bands have different molecular weights that correspond to three N-acetyl amino sugars found in band A and absent in band B.

The protective capacity of the OMVsBpp and the OMVsBp against infection by *B. parapertussis* and the protection conferred by immunization with the OMVs obtained from *B. parapertussis* against the infection caused by *B. parapertussis* are shown.

To evaluate the protective capacity induced by the OMVs prepared from *B. parapertussis* (OMVsBpp) against infection by *B. parapertussis*, assays were carried out in mice which were challenged intranasally with the *B. parapertussis* AR729 strain. In particular, the effect of two doses of OMVsBpp on colonization by *B. parapertussis* ($1 \times 10^7$ CFU per 40 µl) was analyzed. The results obtained were compared with the ones found in immunized mice, either with the OMVs from *B. pertussis* or with the commercial acellular vaccine formulated with antigens of *B. pertussis*. Animals treated with PBS were used as control. The differences observed in counting the bacteria recovered from the lungs of the vaccinated animals compared with the ones belonging to the control animals were significant ($p<0.001$) (FIG. 6).

Mice immunized with the vaccines containing the OMVsBpp displayed adequate rates of bacterial elimination of *B. parapertussis*. The number of bacterial colonies recovered from these mice was reduced in three orders of magnitude compared with the ones found in non-immunized mice (FIG. 6). In animals treated with PBS the number of bacteria recovered was the highest (more than $10^4$ CFU per lung). This protection against *B. parapertussis* was not achieved after immunization with OMVsBp or with the commercial acellular formulation.

The protective capacity of the OMVsBpp and the protection induced by immunization with OMVsBp against the intranasal challenge with *B. pertussis* is shown.

In order to evaluate the protective capacity against *B. pertussis* generated by immunization with OMVs, protection and challenge assays were carried out in the murin model. In particular, the effect of two immunizations with OMVsBp (days 0 and 14) against a challenge with *B. pertussis* ($2 \times 10^7$ CFU per 40 µl) on day 14 of the last immunization was analyzed. The protective capacity of OMVs obtained from *B. parapertussis* AR729 against *B. pertussis* was also analyzed. As a reference, a group of animals immunized with a commercial acellular formulation containing antigens of *B. pertussis* was included. In all cases, the OMVs were detoxified by treatment with formaldehyde. A group treated with PBS was included as control. In all cases, the animals immunized with the different OMVs or with the acellular formulation exhibited a significant reduction in post-challenge colonization, indicating an adequate protector effect against B. pertussis (p<0.001) (FIG. 7).

Interestingly, immunization with OMVsBpp obtained from a different species from the one used for the challenge achieved adequate levels of protection, indicating a strong capacity for cross protection in the case of the OMVsBpp. Immunization with the commercial acellular formulation displayed a strong reduction in the post-challenge bacterial load only for B. pertussis, at least in the order of four orders of magnitude in relation to the negative control (FIG. 7). The commercial acellular vaccine is not protective against the B. parapertussis challenge. The group of animals treated with PBS proved not to be protective and a high number of colonies ($10^5$ CFU per lung) at the time of counting were detected. Cross protection can be attained alternatively by using OMVsBp and the addition of LPS from B. parapertussis. Given that it is highly desirable to obtain a vaccine formulation capable of conferring protection against *B. pertussis* and *B. parapertussis*, another embodiment is shown that allows for attaining this effect. The addition of LPS from *B. parapertussis* to the OMVs obtained from *B. pertussis* generates a formulation with the same protective capacity against both species as the OMVsBpp, as the results from the protection and challenge experiments show (FIG. 8). Neither the OMVsBp nor the commercial acellular formulation display this capacity of providing cross protection.

In the immunization model with intranasal challenge, we were able to show the protective capacity against infection by *B. parapertussis* generated by immunization with the mix of LPS from *B. parapertussis* (LPSBpp) and the OMVs prepared from *B. pertussis* (OMVsBp). In particular, after two immunizations with OMVsBp+LPSBpp (days 0 and 14), the protective capacity against a challenge with *B. parapertussis* ($2\times10^7$ CFU per 40 μl) was analyzed. As a benchmark, a group of animals immunized only with OMVsBp, without adding LPSBpp, and another group only with LPSBpp were included. In all cases, the formulations of OMVs were detoxified by treatment with formaldehyde. A group treated with PBS was included as a negative control for protection. The pulmonary count of *B. parapertussis* on day seven post-challenge was clearly inferior to the groups immunized only with OMVsBp+LPSBpp or LPSBpp, in relation to the control group ($p<0.001$) (FIG. 8). The rate of elimination observed in the groups immunized with OMVsBp+LPSBpp or LPSBpp indicates a high degree of protection ($p<0.001$), with a drop of at least three orders of magnitude in the bacterial count in relation to the negative control (FIG. 8). The group immunized with OMVsBp and the group treated with PBS showed a high count of *B. parapertussis* on day seven post-challenge ($10^4$ CFU per lung).

Furthermore, when an immunization scheme similar to the previous experiment was maintained, but a challenge was performed with *B. pertussis*, it was seen that LPSBpp is not capable of conferring protection against this other species. Only animals immunized with OMVs obtained from *B. pertussis* or with OMVsBp+LPSBpp were protected against a challenge with *B. pertussis* (FIG. 9).

All these results indicate the protective capacity of LPSBpp against the infection with *B. parapertussis*. LPSBpp would be one of the main components responsible for the protective capacity against this species.

Acellular Vaccines Comprising OMVs from *Bordetella:*

The protective capacity of combined vaccines containing OMVsBpp, tetanus and diphtheria toxoids (acellular vaccine $Tdap_{OMVsBpp}$) induces protection against infection caused by *B. parapertussis* and by *B. pertussis*. Consequently, it was assessed by means of animal assays using the intranasal bacterial challenge. In particular, the effect of administering two doses of Tdap (OMVsBp+OMVsBpp) or Tdap (OMVsBpp) on colonization of *B. parapertussis* ($1\times10^7$ CFU per 40 μl) was analyzed. In all cases, the immunogens were detoxified by treatment with formaldehyde. A control group treated with PBS was included. Significant differences in the bacterial count of the lungs were observed between the Tdap (OMVsBp+OMVsBpp) or Tdap (OMVsBpp) treatments and the control group ($p<0.001$) (FIG. 10).

Adequate rates of bacterial elimination in mice immunized with Tdap (OMVsBp+OMVsBpp) or Tdap (OMVsBpp) ($p<0.001$) were observed. For these treatments, the number of colonies of *B. parapertussis* recovered from the lungs on day seven post-challenge was reduced by at least three orders of magnitude in relation to the ones found in the non-immunized controls (FIG. 10). The highest count values were registered in mice treated with PBS ($10^5$ CFU per lung).

Adequate rates of bacterial elimination were observed when the mice were challenged with *B. pertussis* 18323 (FIG. 11).

Toxicity assays were performed using the weight gain test, commonly used to measure the toxicity of formulations against whooping cough. For the assays, mice were weighed at 16 h and on days 3 and 7 after immunization. All the formulations used here for vaccination did not alter the weight gain curve, which means that the formulations are not toxic.

Generally, after systemic immunization, an increase in proinflammatory cytokines can be detected. The levels are related to the proinflammatory capacity of the formulation being used. IL-6 is one of the proinflammatory cytokines usually used as an indicator of this activity. In this case, the capacity to induce IL-6 in the different formulations was analyzed. A representative result is displayed in FIG. 12. In all cases, formulations containing OMVsBpp, formulated as Tdap or as a vaccine with OMVs as a single component, induced the lowest levels of IL6 compared with formulations containing OMVsBp (also formulated as Tdap or as a monovalent vaccine).

Another representative result is shown in FIG. 13. Mice immunized with the commercial Tdap and with the cellular vaccine used in the vaccination schedule in force in Argentina (the bacterial quadruple vaccine DTP+Hib made up of diphtheria and tetanus toxoids and whole bacteria of *B. pertussis* killed by heat and detoxified, and of purified immunogens of type B Haemophilusinfluenzae) were added as controls. In all cases, the formulations containing OMVs and the acellular vaccine induced lower levels of IL6 in comparison with the cellular vaccine (FIG. 13). Tdap formulations containing OMVs from *B. pertussis* induced higher levels than the one formulated only with OMVs from *B. parapertussis.*

A combined Tdap vaccine was formulated containing the two OMVs and the tetanus and diphtheria toxoids Tdap (OMVsBp+OMVsBpp).

Protection assays for dose-response were performed, using a protection model on mice as described in the examples. In particular, the effect on colonization of *B. pertussis* ($1\times10^7$ CFU per 40 μl) of Tdap was analyzed, whereby 3 combinations of OMVs were assayed where the quantity of OMVsBpp was maintained at 9 μg of proteins and the quantity of OMVs from *B. pertussis* was varied. Specifically in the assayed Tdaps, the OMVs from *B. parapertussis* (9 μg) were combined with 3; 1.5 and 0.75 μg of OMVs from *B. pertussis*. Tdap vaccines containing OMVs from *B. parapertussis* are less toxic and protect against *B. parapertussis* and *B. pertussis*, and the OMVs from *B. pertussis* protect more against *B. pertussis* than the ones containing only OMVs from *B. parapertussis* and, although they have proven biosafe in toxicity tests, they are a bit more toxic than Tdap formulations containing OMVs from *B. parapertussis*. Based on these properties, we have formulated Tdap vaccines, increasing the amount of OMVs from *B. parapertussis* and decreasing the OMVs from *B. pertussis*. The results obtained were compared with the ones found in mice immunized either with the Tdap vaccines and with formulations exclusively containing OMVs from *B. pertussis* in the different doses assayed (3; 1.5 or 0.75 μg), or exclusively with OMVs from *B. parapertussis* in doses similar to the ones pertaining to combined vaccines (9 μg). For the toxicity tests, we also included the commercial acellular vaccine against *B. pertussis* and the commercial cellular vaccine.

Animals treated with PBS were used as a negative control for protection. The differences observed in the counting of bacteria recovered from the lungs of the vaccinated animals in relation to bacteria retrieved from the control animals were significant ($p<0.001$) (FIG. 14).

In all cases, immunization performed with Tdap formulations containing in their composition OMVs from *B. parapertussis* are expected to provide complete protection against *B. parapertussis* as we have demonstrated that such formulations, even if they contain less quantities than the ones assayed previously (3 μg instead of 9 μg), are on their own highly immunoprotective against colonization by *B. parapertussis*.

Mice immunized with Tdap vaccines containing OMVs, whether from *B. pertussis* or *B. parapertussis*, or combinations thereof, exhibited adequate bacterial elimination rates except for vaccines containing OMVs from *B. pertussis* at a concentration of 0.75 μg per dose. The number of bacterial colonies recovered from those mice, except for mice immunized with Tdap containing only OMVs from *B. pertussis* at a concentration of 0.75 μg per dose, fell by three orders of magnitude in relation to the ones found in unimmunized mice (FIG. 14). In animals treated with PBS, the number of bacteria recovered was the highest (more than $10^5$ CFU per lung).

Protection and toxicity results place the vaccines of the invention containing OMVs in an advantageous position. In particular, Tdap vaccines made up of combinations of OMVsBp and OMVsBpp are better as compared with other existing vaccines, since they provide protection against two species of the *Bordetella* genus and with very low levels of toxicity. The combination of the Tdaps of OMVs from *B. parapertussis* in concentrations of 9 μg per dose+OMVs from *B. pertussis* in concentrations of 0.75 μg per dose renders excellent levels of protection and very low toxicity. The combination of the Tdaps of OMVs from *B. parapertussis* in concentrations of 9 μg per dose+OMVs of *B. pertussis* in concentrations of 3 μg per dose induces excellent levels of protection and very good toxicity parameters. It is noteworthy that all Tdap formulations comply with WHO criteria for the weight loss test. Formulations that include higher doses of OMVsBp, although they surpass toxicity criteria, exhibit IL 6 values that are a bit higher than the 9 μg OMV Bpp+0.75 μg OMV Bp formulation.

To further our knowledge of the protective capacity of the Tdap vaccines containing OMVs, the long-term protective capacity of the Tdap OMVsBp vaccine was assessed. Thus, a two-dose immunization procedure was performed as described in FIG. 15 and the long-term protective capacity of the treatment was assessed in comparison with an intranasal challenge with *B. pertussis*, performed on month 5 or month 9 post-immunization (FIGS. 15 and 16). These results indicate that the Tdap OMVsBp formulation maintains a long-term protective capacity, providing protection for several months after immunization is performed. Assay time implies a protective capacity that covers more than half the average life span of the animals used.

FIG. 17 illustrates that the Tdap vaccines containing OMVsBp are capable of providing protection against infections produced by different genetic backgrounds of *B. pertussis*: Bp18323, BpTohama and Bp106 (Argentine isolation). These results, exhibited in FIG. 17, indicate that the Tdap OMVsBp formulation maintains a protective capacity against different challenges performed with the various suspensions. These results position Tdaps containing OMVs over current commercial acellular vaccine because of their broad range in protecting against different strains, some pertaining to the current circulating bacterial population.

This invention is better illustrated according to the following examples, which should not be construed in any way as a limitation on the scope thereof. On the contrary, it should be clearly understood that other embodiments, modifications, and equivalents thereof can be resorted to, which after reading the description herein, may arise to those skilled in the art without departing from the spirit of this invention and/or the scope of the appended claims.

EXAMPLES

Example 1

Bacterial Strains and Culture Conditions

Strains of *B. pertussis* Tohama (CIP 8132), *B. pertussis* 18323 and *B. parapertussis* AR729 were used throughout this work. Strains of *B. pertussis* and *B. parapertussis* are cultured in the synthetic medium of Stainer-Scholte liquid medium (SS) as reported previously (Stainer, D. W., et al. J. Gen. Microbiol. 63:211-20, 1970).

Isolation of Outer Membrane Vesicles (OMVs):

To obtain the OMVs from bacterial cells, the method described previously, with some slight modifications, was used (Hozbor, D., et al, Curr. Microbiol. 38:273-278, 1999; Roberts, R., G. et al, Vaccine 26:4639-464617-18, 2008; and Asensio, C. J., et al, Vaccine 29:1649-165621, 2011). In brief, bacteria growing in the synthetic medium SS were harvested by centrifugation and resuspended in 20 mMTris-HCl, 2 mM EDTA pH 8.5 (TE buffer). Five milliliters of TE buffer are used to resuspend approximately 1 g (wet weight) of the bacteria. The bacterial suspension obtained thus is subjected to ultrasound in cold water for 20 min. After three centrifugations at 10,000 g for 20 min at 4° C., the supernatant sediments at 100,000 g for 2 hours at 4° C. This sediment is resuspended in 20 mMTris-HCl, pH 7. When several months of storage are required, the OMVs obtained thus are stored in 1% glycerol and 0.001% sodium azide at 4° C. The samples obtained from the cells are stained negatively and then examined by electron microscopy.

Electron Microscopy:

Electron microscopy of the OMVs is performed on 0.1 M of ammonium acetate (pH 7.0). A drop of this suspension is placed on a grid coated with a carbon film reinforced with fomvar. After 30 s, the excess liquid is removed by absorption with a paper filter and the grids are stained with 2% (w/v) phosphotungstic acid (pH adjusted to 5.2 with KOH). A Jeol JEM 1200 EX microscope was used for examining.

Determination of Proteins:

The protein content is estimated by the Bradford method using bovine serum albumin as a standard protein. Proteins that constitute the membrane vesicles are separated in two-dimensional gels (2D electrophoresis). Proteins that constitute the vesicles are identified by mass spectrometry associated with 2D electrophoresis (for further details of the methodology, please see: Bottero, D., et al, J. Appl. Microbiol. 112:1266-1276, 2012 and Bottero, D., et al, Clin. Vaccine Immunol. 14:1490-1498, 2007). The identified proteins are listed in Tables 1 and 2.

Extraction and Electrophoretic Run (SDS-PAGE) of Lipooligosaccharide (LOS) and Lipopolysaccharide (LPS):

The LOS of the OMVs from *B. pertussis* and the LPS of the OMVs from *B. parapertussis* are solubilized in a running buffer and heated at 100° C. for 10 min. Twenty-five micrograms of proteinase K in 10 μl of buffer are added for every 50 μl of suspension of LOS/LPS. The mixes obtained thus are incubated in a water bath at 60° C. for 1 h. The samples treated with the proteinase K are resolved on polyacrylamide gels. Electrophoresis is run at room temperature and at a constant voltage. The LOS/LPS are visualized by silver staining (BioRad technique).

Reproducibility of the Methodologies

The outer membrane vesicles of *B. pertussis* and *B. parapertussis* were obtained by means of the procedure described above at least twenty times and in all cases the immunogens, sizes, and morphology were the same.

Formulation of the Acellular Vaccines Containing OMVs of *Bordetella*

Monovalent Vaccines (Also Called Single Component Vaccines)

In order to use the OMVs of *B. pertussis* or *B. parapertussis* as monovalent vaccines, the vesicle preparations are emulsified with aluminum hydroxide as an adjuvant (0.2 mg/ml) and detoxified with formaldehyde (0.37% at 37° C. overnight).

Multivalent or Combined Vaccines (Tdap)

Each one of the vesicles (in the quantities specified below) obtained from *B. pertussis* and/or *B. parapertussis* are formulated with diphtheria and tetanus toxoids in the quantities described below, in addition to the aforementioned aluminum hydroxide. These formulations known as Tdap contain:

Active Principles:

diphtheria toxoid, tetanus toxoid. OMVs obtained from *B. pertussis* and/or *B. parapertussis*

Storage conditions. Preservation between 2° C. to 8° C.

Appearance: Uniform (white suspension without foreign particles)

pH: between 6.7 to 7.3

Tetanus toxoid: 5 to 7 Lf/dose with a potency higher or equal to 2 UIA/ml of serum Diphtheria toxoid: 1 to 3 Lf/dose with a potency of 0.1 UIA/ml of serum The OMV of *B. pertussis* (3 μg of total OMV protein) [in this case, the combined vaccine was named Tdap (OMVsBp)] or the OMV of *B. parapertussis* (3 μg or the amount specified) [in this case, the multivalent vaccine was named Tdap (OMVsBpp)] or two [in this case, the multivalent vaccine was named Tdap (OMVsBp+OMVsBpp)]. Other concentrations of OMVs were assayed, a list of which can be found in the legend of the figures.

The aluminum content in all cases was not higher than 1.25 mg/dose.

Example 2

Protection Assays Using the Intranasal Challenge Model on Mice

Immunization by Systemic Routes with Intranasal Challenge.

Four-week-old female BALB/c mice were used for these assays. The mice were obtained from Biol. SAIC, Argentina.

Groups of 10 to 15 BALB/c mice were immunized with the formulations previously described. The immunization protocols involve a regimen of two doses i.p. separated by a two-week period. The mice were challenged two weeks after the second immunization with a sublethal dose ($10^6$-$10^8$ UFC 40 μl) of the strains of *B. pertussis* or of *B. parapertussis* as indicated in the figures.

The lungs of the exposed mice were collected for the bacterial count on day seven after the challenge. The lungs, aseptically obtained, were homogenized in sterile PBS, serially diluted and then spread on Bordet-Gengou plates supplemented with defribinated ram blood for the number of colonies recovered. At least three independent experiments were carried out in each case.

Weight Gain Testing

In this test, eight Balb/c mice (15-20 g) vaccinated with any of our formulations obtained from strains of *B. pertussis* and *B. parapertussis* were used. In all cases, the control group received the same volume as the vaccine suspensions, albeit of sterile PBS. The animals are observed for seven days and the body weight is registered at 16 h and on days 3 and 7 post-challenge. The vaccines are considered non-toxic when they meet the following requirements (WHO and EP requisites): (a) the total weight of the mice from the vaccinated group on day 3 after treatment should be the same or higher than baseline weight; (b) on day 7 average weight gain of the vaccinated group should not be less than 60% of the control group's; and (c) the death rate should be no higher than 5% during the period under analysis.

Expression of Inflammation Markers after Systemic Treatment with the Formulations Containing OMVs and Toxicity Assessment With the purpose of having an additional indication of pro-inflammation among the different formulations, sera by submandibular bleeding was collected 4 hours after each immunization. The IL-6 levels were measured by ELISA in the obtained sera using BD OptiEIA (BD Biosciences) according to the manufacturer's instructions.

Long-Term Protective Immunity

To analyze long-term protective immunity, mice immunized according to the schedule shown in FIG. 15 were challenged on month 2, 5 and 9 after the second immunization with sublethal doses ($10^6$-$10^8$ CFU 40 μl-1) of *B. pertussis*. In all cases, bacterial counting took place seven days after the challenge. The lungs were removed aseptically, homogenized in sterile PBS, diluted serially and then plated on BGA to ascertain bacterial recoveries. At least three independent experiments were carried out in each case. Groups of mice treat with a PBS buffer were used as a negative control for protection. Results obtained from high doses of commercial acellular vaccines were included.

Statistical Analysis The data was analyzed using a unidirectional analysis of variance (ANOVA), followed by Bonferroni's multiple comparison (GraphPadPrims®). Difference were considered to be significant whenever $p<0.05$.

What is claimed is:

1. A vaccine for the prevention of infections with *Bordetella*, comprising outer membrane vesicles (OMVs) from *B. pertussis*, outer membrane vesicles (OMVs) from *B. parapertussis*, 5 to 7 Lf per dose of tetanus toxoid, 1 to 3 Lf per dose of diphtheria toxoid, and less than 1.25 mg per dose of aluminum hydroxide.

2. The vaccine according to claim 1, comprising between 0.75 and 3 µg of outer membrane vesicles (OMVs) from *B. pertussis*, between 3 and 9 µg of outer membrane vesicles (OMVs) from *B. parapertussis*, 5 to 7 Lf per dose of tetanus toxoid, 1 to 3 Lf per dose of diphtheria toxoid, and less than 1.25 mg per dose of aluminum hydroxide.

* * * * *